(12) United States Patent
Purea et al.

(10) Patent No.: US 10,197,653 B2
(45) Date of Patent: Feb. 5, 2019

(54) MAS STATOR OF AN NMR PROBE HEAD WITH OPTIMIZED MICROWAVE IRRADIATION

(71) Applicant: Bruker BioSpin GmbH, Rheinstetten (DE)

(72) Inventors: Armin Purea, Bad Schoenborn (DE); Arndt Von Bieren, Munich (DE)

(73) Assignee: BRUKER BIOSPIN GMBH, Rheinstetten (DE)

( * ) Notice: Subject to any disclaimer, the term of this patent is extended or adjusted under 35 U.S.C. 154(b) by 93 days.

(21) Appl. No.: 15/591,779

(22) Filed: May 10, 2017

(65) Prior Publication Data

US 2018/0113183 A1 Apr. 26, 2018

(30) Foreign Application Priority Data

May 10, 2016 (DE) .......................... 10 2016 207 998

(51) Int. Cl.
*G01V 3/00* (2006.01)
*G01R 33/46* (2006.01)
(Continued)

(52) U.S. Cl.
CPC .......... *G01R 33/4616* (2013.01); *G01B 7/30* (2013.01); *G01R 1/067* (2013.01); *G01R 33/282* (2013.01);
(Continued)

(58) Field of Classification Search
CPC .................................................. G01R 33/307
(Continued)

(56) References Cited

U.S. PATENT DOCUMENTS 6,060,882 A * 5/2000 Doty ................ G01R 33/34046
324/318
2014/0099730 A1 4/2014 Hu
(Continued)

FOREIGN PATENT DOCUMENTS

JP 2011158348 A 8/2011
JP 201226886 A 2/2012
(Continued)

OTHER PUBLICATIONS

Nanni et al., "Microwave field distribution in a magic angle spinning dynamic nuclear polarization NMR probe", Journal of Magnetic Resonance 210, 2011, pp. 16-23.
(Continued)

*Primary Examiner* — Louis Arana
(74) *Attorney, Agent, or Firm* — Edell, Shapiro & Finnan, LLC

(57) ABSTRACT

An NMR probe head with an MAS stator (1) supplied with microwave radiation from a microwave guide (9) through an opening in a coil block (2) has a microwave lens (6) and a microwave mirror (8*a*) on an inner side of the MAS stator. The MAS rotor (3) is surrounded by a solenoid RF coil (5) and the microwave lens is arranged and embodied in the opening of the coil block on the side facing a sample volume (4) such that the cylinder axis of the MAS rotor lies in the focus of the microwave lens. The microwave mirror is arranged on, or in, the inner wall of the MAS stator that lies opposite the microwave guide and has a cylindrical and concave structure, such that the microwave mirror focuses the microwave radiation incident from the sample volume onto the central axis of the MAS rotor.

21 Claims, 3 Drawing Sheets

(51) Int. Cl.
*G01B 7/30* (2006.01)
*G01R 1/067* (2006.01)
*G01R 33/30* (2006.01)
*G01R 33/34* (2006.01)
*G01R 33/28* (2006.01)
*G01N 24/12* (2006.01)
*G01R 33/62* (2006.01)

(52) U.S. Cl.
CPC ......... *G01R 33/302* (2013.01); *G01R 33/307* (2013.01); *G01R 33/34053* (2013.01); *G01N 24/12* (2013.01); *G01R 33/62* (2013.01)

(58) Field of Classification Search
USPC .................................................. 324/321, 318
See application file for complete search history.

(56) References Cited

U.S. PATENT DOCUMENTS

| | | |
|---|---|---|
| 2014/0117988 A1 | 5/2014 | Annino et al. |
| 2015/0010255 A1 | 1/2015 | Ishida |
| 2016/0195593 A1* | 7/2016 | Purea .................. G01R 33/282 324/322 |
| 2016/0334476 A1* | 11/2016 | Doty .................... G01R 33/282 |

FOREIGN PATENT DOCUMENTS

| | | |
|---|---|---|
| JP | 2014518384 A | 7/2014 |
| WO | 2015107512 A1 | 7/2015 |
| WO | 2015175507 A1 | 11/2015 |

OTHER PUBLICATIONS

Emilio A. Nanni et al., "Microwave field distribution in a magic angle spinning dynamic nuclear polorization NMR probe", Journal of Magnetic Resonance, vol. 210, No. 1, Mar. 5, 2011.

Barnes A. B. et al., "Cryogenic sample exchange NMR probe for magic angle spinning dynamic nuclear polarization", Journal of Magnetic Resonance, Academic Press, Orlando, FL., vol. 198, No. 2, Mar. 17, 2009.

Rosay Melanie et al., "Instrumentation for solid-state dynamic nuclear polarization with magic angle spinning NMR" Journal of Magnetic Resonance, Academic Press, Orlando, FL., vol. 264, No. 23, Feb. 23, 2016.

Kent R. Thurber et al., "Solid state nuclear magnetic resonance with magic-angle spinning and dynamic nuclear polarization below 25K", Journal of Magnetic Resonance., vol. 226, No. 21, Nov. 2012.

* cited by examiner

PRIOR ART

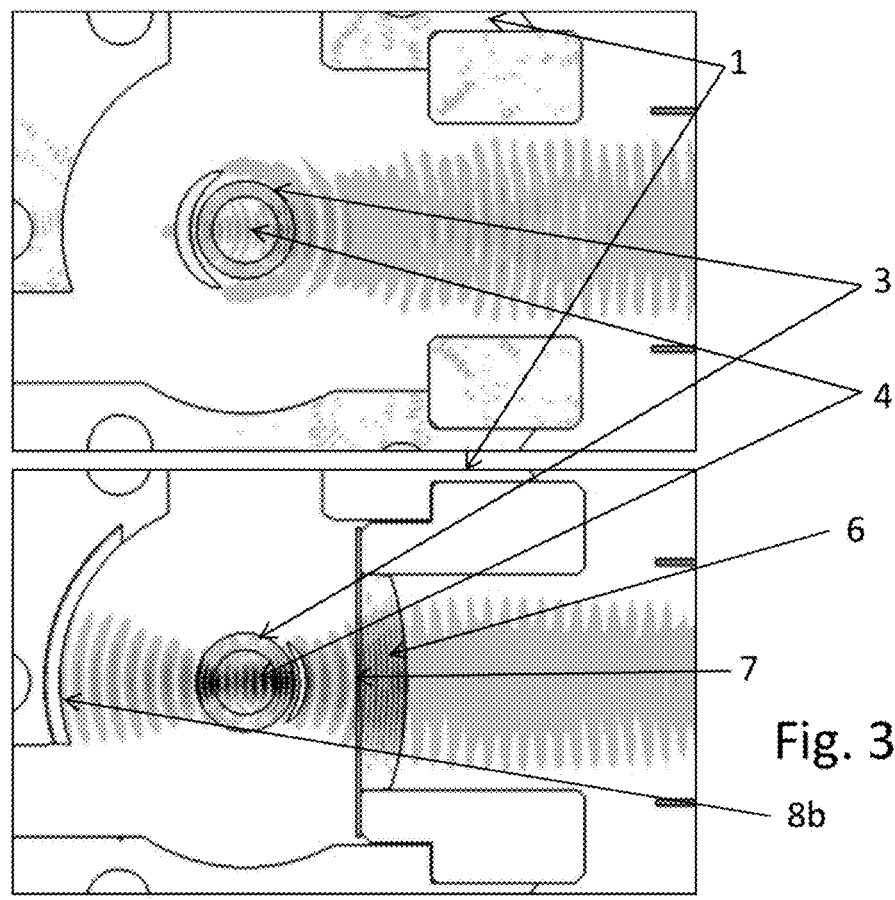
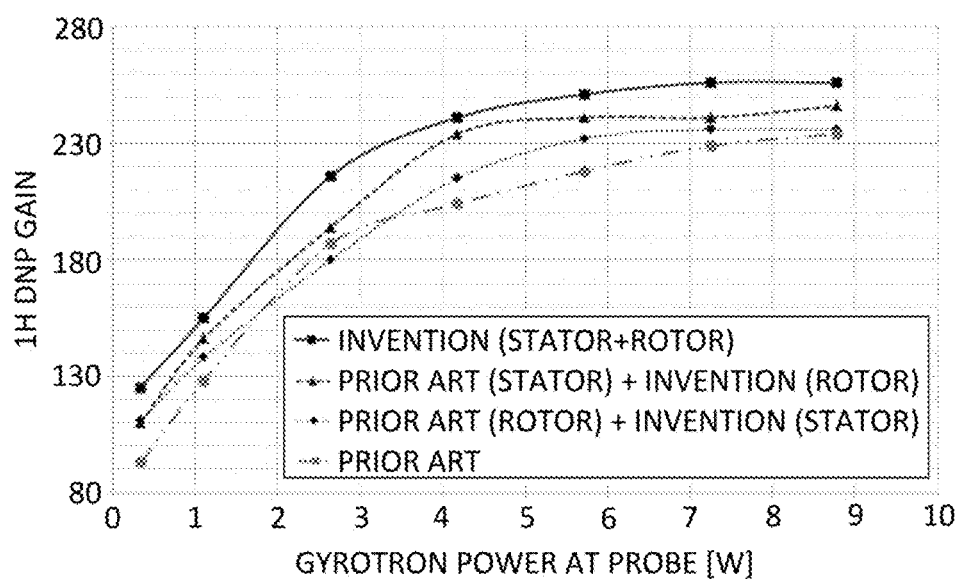
Fig. 3
Fig. 4

MAS STATOR OF AN NMR PROBE HEAD WITH OPTIMIZED MICROWAVE IRRADIATION

CROSS REFERENCE TO RELATED APPLICATIONS

This application claims the benefit of and foreign priority under 35 U.S.C. § 119(a)-(d) to German Patent Application No. 10 2016 207 998 filed on May 10, 2016, which is incorporated in its entirety into the present application by reference.

FIELD OF THE INVENTION

The present invention relates to the field of magnetic resonance (MR). More specifically, the invention relates to an MAS stator of an NMR probe head.

BACKGROUND

Nuclear magnetic resonance (NMR) spectroscopy is a commercially widespread method in MR for characterizing the chemical composition of substances. In MR, the measurement sample which is situated in a strong static magnetic field is generally irradiated by radiofrequency (RF) pulses and the electromagnetic reaction of the sample is measured. Further, it is known in solid-state NMR spectroscopy to rotate an NMR sample tilted at the so-called "magic angle" of approximately 54.74° in relation to the static magnetic field during the spectroscopic measurement ("MAS"=Magic Angle Spinning) in order to minimize line broadening on account of anisotropic interactions. To this end, the sample is inserted into an MAS rotor. MAS rotors are cylindrical tubes which are sealed with one or two caps, the upper one being provided with blade elements ("impeller"). The MAS rotor is arranged in an MAS stator and the MAS rotor is driven for the purposes of the rotation by gas pressure by way of the blade elements. The totality of MAS rotor and MAS stator is referred to as MAS turbine.

The MAS turbine is arranged in an NMR-MAS probe head during the NMR measurement. The probe head comprises a cylindrical shielding tube. Housed therein are RF electronic components, in particular RF coils, and the MAS turbine. With the shielding tube thereof, the probe head is typically inserted from below into the vertical room temperature bore of a superconducting magnet, positioned therein and held therein with hooks, supports, screws or the like. The MAS turbine is then situated precisely in the magnetic center of the magnet.

In addition to solid-state NMR, use may also be made of the dynamic transfer of spin polarization (DNP=dynamic nuclear polarization) technique. The DNP technique requires simultaneous irradiation of a magnetic microwave field at a frequency which is higher than the Larmor frequency of the 1H nuclei by a factor of 660. Electron spins are excited by irradiation of a microwave field at a suitable frequency, whereupon a transfer of electron polarization onto the atomic nuclei of the sample may be brought about on account of spin interactions.

Currently, microwave radiation is irradiated into the MAS stator simply through a round hole in the coil block through the RF coil, optionally with a suitable widening of the coil windings at the center, without further measures being undertaken. However, when using this technique, only a fraction of the introduced power reaches the alternating magnetic field at the location of the sample.

Although the article Nanni et al., Journal of Magnetic Resonance 210 (1), 2011, 16-2 describes individual constituents of a generic apparatus such as lens, coil windings, rotor wall thickness, mirror, etc. per se, it does not describe a suitable combination and common optimization thereof. Moreover, the tunability to different samples is not taken into consideration.

WO 2015/107512 A1 likewise relates to an increase in the millimeter wave field for DNP, but on a static, i.e. non-rotating, basis. The MAS technique is only mentioned as a further goal. Moreover, use is not made of a lens here either; instead, use is made of a resonator-like structure.

WO 2015/175507 A1 discloses an NMR-DNP-MAS probe head for receiving a substantially circular-cylindrical hollow MAS rotor with a sample substance in a sample volume. This MAS rotor may be mounted with pressurized gas in a measuring position within the MAS stator with a device for gas supply and set into rotation about the cylinder axis of the MAS rotor with a pneumatic drive. A hollow microwave guide supplies microwave radiation into the sample volume through an opening in a coil block introduced into the wall of the MAS stator. A microwave lens is arranged between the microwave guide and the sample volume for focusing the supplied microwave radiation onto the MAS rotor. The MAS rotor is surrounded by a solenoid RF coil and a microwave mirror for reflecting the microwave radiation emerging from the microwave guide and passing through the sample volume is provided on the inner side of the MAS stator lying opposite the microwave guide. The field distribution shown in FIG. 10C of that reference implies that the known arrangement produces a tunable resonator. The adjustable mirror shown therein is intended to tune a "cavity mode". Furthermore, FIG. 10C of said document shows that the wavelength corresponds to approximately twice the rotor diameter. For a 3.2 mm system, this means a vacuum wavelength of approximately 6 mm and hence a frequency of 50 GHz. Actually, said wavelength would be even shorter in matter, and so the illustration in FIG. 10C is physically unrealistic whenever the rotor and the measurement sample have a dielectric constant >1; this can usually be assumed.

While such a strongly resonant structure has the advantage of a high field amplitude, a fundamental disadvantage of such resonators lies in that the high quality which is usually obtainable requires a very narrow frequency bandwidth which reacts very sensitively to external or internal influences and therefore requires very precise tuning.

SUMMARY

In contrast thereto, an object of the present invention is to make available an MAS stator for an NMR-DNP-MAS probe head of the type defined at the outset which significantly increases the irradiation efficiency, i.e. the magnetic field strength per unit of power radiated in, in the MAS rotor of the probe head at the location of the sample in a frequency range (generally 200-600 GHz) typical for exciting the electron spins within the scope of the DNP technique.

This object is achieved by an MAS stator of the type set forth at the outset, wherein the microwave lens has a focal length and is arranged in the opening of the coil block on the side facing the sample volume such that the cylinder axis of the MAS rotor lies in the focus of the microwave lens.

Preferably, the microwave lens is configured to have a thickness on the central axis thereof that is an integer multiple of half the wavelength of the microwave radiation transmitted in the dielectric of the microwave guide such that the microwave radiation incident from the microwave guide is transmitted maximally in the direction toward the sample volume. The RF coil is a single-layer solenoid coil constructed from a plurality of spaced-apart windings, the winding wire thickness d and the winding spacing D of which are optimized in such a way that at least 80% of the microwave radiation is transmitted through the RF coil, wherein the ratio of d to D is less than or equal to 0.5 and the ratio of D to the wavelength of the microwave radiation in vacuo is greater than 0.5, preferably close to 1. The microwave mirror is arranged on, or in, the inner wall of the MAS stator lying opposite the microwave guide with respect to the sample volume and is constructed cylindrically and in a concave shape in the direction toward the sample volume. From a structural point of view, the microwave mirror is configured to focus the microwave radiation which comes from the sample volume and is incident on the mirror onto the central axis of the circular-cylindrical MAS rotor.

The present invention provides a stator for NMR-DNP-MAS spectroscopy which facilitates an improved yield of the incident microwave power by virtue of a plurality of components being combined in a novel and surprising fashion. The lens not only focuses the beam onto the sample but also, at the same time, brings the beam perpendicularly onto the curved rotor surface. As a result, the optical path through the rotor wall becomes equally long for the entire beam such that the thickness of the rotor wall may be set such that a portion of the radiation which is as large as possible is transmitted. In this respect, the coil is a bothersome component since, depending on the embodiment thereof, it may lead to diffraction and scattering of the beam. For the purposes of maintaining the beam characteristic, the coil is therefore dimensioned in the manner described above such that there is no notable scattering or diffraction, even after several passages through the coil. If a mirror is additionally placed against the stator rear wall, likewise in such a way that the focus thereof lies in the center of the rotor, a renewed passage of the beam through the sample is achieved, as a result of which a larger proportion of the introduced power may act in the sample.

In contrast to the prior art discussed above, the present invention achieves a skillful focusing of the microwave radiation onto the sample using a quasi-optical structure and, in the process, obtains such a beam characteristic that a second passage through the sample is facilitated after reflection at a suitable mirror. In this respect, the present structure according to the invention should be classified as an only weakly resonant structure. However, it is therefore also more robust.

A decisive advantage of the combination of features according to the invention lies in the fact that each individual improvement can actually make its contribution. If the combination proposed by way of the invention is not selected, it may be the case that an individual feature is not able to achieve its full potential. The mirror, for example, would be an example thereof: without a suitable lens, an adapted coil and an adapted rotor wall, hardly any of the radiation is cast back through the sample since the beam is scattered too strongly and reflected in an inexpedient manner.

A further advantage of the present invention lies in the fact that the available, customary MAS stator need hardly be modified and the additional parts only require very little material outlay such that the teaching according to the invention may be implemented in a very cost-effective manner.

In particularly preferred embodiments of the MAS stator according to the invention, the microwave lens has a plano-convex form as seen in the beam direction of the microwave radiation emerging from the microwave guide in the direction toward the sample volume and, preferably, a thickness of between 1 mm and 2 mm, in particular approximately 1.5 mm, on the central axis thereof. This brings about a change in the irradiation of the sample such that the incident beam impinges perpendicularly on the rotor wall such that the rotor wall thickness may be set for ideal transmission (like a planar layer).

In practice, embodiments of the invention in which the microwave lens has at least one cylindrical area, in particular with a radius of curvature of between 8 mm and 15 mm, preferably of approximately 11.5 mm, have been found to be particularly useful. As a result, the lens is embodied as a converging lens with a comparatively large radius on account of the high refractive power (see below) such that the thickness is small in comparison with the dimensions in the other two directions.

Moreover, the microwave lens is constructed from dielectric material, preferably from sapphire and/or silicon and/or boron nitride, in preferred embodiments of the probe head according to the invention. These materials cause only small losses (tan d≤0.001) and produce a high refractive power, even for thin lenses (see above).

Embodiments of the invention in which an antireflection coating preferably made of plastic, in particular made of PTFE or Vespel, or made of a sub-wavelength structure is applied to the outer surfaces of the microwave lens are also preferred. Such an antireflection coating maximizes the transmission of the incident beam through the lens.

A further preferred embodiment provides for the RF coil to be constructed from a magnetically compensated wire or from Cu and/or Ag and/or Al or the alloys thereof. This keeps field distortions as a result of the RF coil low and facilitates a sufficiently good spectral resolution (<~a few Hz in the NMR experiment).

Embodiments of the MAS stator according to the invention in which the RF coil is constructed with a winding wire thickness d of 0.2 mm to 0.5 mm, in particular d≈0.3 mm, with 5 to 10 windings, in particular 7.5 windings, and with a winding spacing D of 0.7 mm to 2 mm, in particular D≈1 mm, are also preferred. Here, these are typical wire thicknesses for NMR coils with a sufficiently high sensitivity.

In one class of advantageous embodiments of the MAS stator according to the invention, the microwave mirror is constructed from Ag, Au or Cu sheet, which preferably has a thickness between 1 μm and 100 μm, in particular approximately 70 μm. A thin sheet made of the aforementioned materials minimizes the static and RF field distortion, while the microwave radiation is completely reflected on account of the low skin depth.

A further class of compact embodiments of the invention with a particularly simple structure is distinguished by virtue of the microwave mirror being rigidly applied, in particular adhesively bonded, soldered or welded, on the inner wall of the MAS stator lying opposite the microwave guide in respect of the sample volume. In this way, the beam is reflected back into the sample volume again.

In a class of embodiments of the MAS stator according to the invention provided as an alternative thereto, said class requiring a little more outlay during production but being significantly more flexible to handle in return, the microwave mirror is introduced in adjustable, in particular displaceable, fashion into the inner wall of the MAS stator lying opposite the microwave guide in respect of the sample volume. By adjusting the distance from the rotor, it is possible to maximize the transmission into the sample volume for different dielectric constants of the sample. However, in contrast to the tuning of the "cavity mode" in the closest prior art, it is the case here that a field strength in the sample which still corresponds to simple passage is achieved even in the least expedient position of the mirror. Hence, there is no risk of complete detuning.

Furthermore, an embodiment in which the MAS stator is rotatably mounted for setting the MAS angle is advantageous. The rotatability of the stator in the probe head may further ease the introduction and removal of the MAS rotor in the case of restricted space; narrow curves are avoided. As a result of the rotatability of the stator, the angle of the stator mounting axis, for loading and unloading purposes, may be reduced in relation to the direction of longitudinal extent of the tube (which regularly corresponds to the direction of the static magnetic field in the NMR magnet, at least to a good approximation) when compared with the magic angle.

The scope of the present invention also includes a probe head comprising an MAS stator of the above-described type according to the invention, in which a pneumatic sample interchange system comprising a transport line is provided for guiding an MAS rotor to and from the MAS stator, likewise contributing to the automation of the measurement preparations and eased progress of MAS-NMR experiments by minimizing the sample interchange times.

The advantages of the present invention take effect in a particularly expedient manner if an MAS rotor with a diameter of from 0.7 mm to 4 mm, preferably from 1.3 mm to 3.2 mm, is used in the probe head according to the invention. Currently, the applicant offers rotors for generic MAS-DNP probe heads in this range.

Preferably, the hollow MAS rotor has a geometric embodiment such that the wall thickness thereof corresponds to an integer multiple of half the wavelength of the transmitted microwave radiation in the dielectric of the rotor wall such that the microwave radiation emerging from the microwave lens is transmitted maximally in the direction toward the sample volume, out of the sample volume and onto the microwave mirror. This renders it possible to minimize the reflection and maximize the transmission through the rotor wall.

In practice, embodiments of the probe head according to the invention, in which the MAS rotor is constructed from sapphire, tetragonally stabilized zirconium oxide and/or silicon nitride, having a wall thickness between 0.2 mm and 0.7 mm, preferably approximately 0.3 mm and 0.55 mm, and having a diameter of less than 4 mm, in particular approximately 3.2 mm, approximately 1.9 mm or approximately 1.3 mm, have proven particularly effective. These materials are particularly suitable for MAS-DNP-NMR as they are non-magnetic, have sufficient mechanical rigidity in order to withstand the forces occurring in the case of rotation and it is possible to set the wall thickness thereof for maximum transmission in the aforementioned manner.

Further advantages of the invention emerge from the description and the drawing. The features mentioned above and the features yet to be explained below may also, according to the invention, be used on their own in each case or together in any combination. The shown and described embodiments should not be understood to be a complete list but, instead, have an exemplary character for explaining the invention.

BRIEF DESCRIPTION OF THE DRAWINGS

The invention is illustrated in the drawing and will be explained in more detail on the basis of exemplary embodiments. In the figures:

FIG. 3 shows a central section through the H-field amplitude distribution of a 3D EM simulation in an arrangement according to the prior art (top) and in an arrangement according to the invention (bottom), wherein the scaling of both field values was selected to be the same; and FIG. 4 shows a graph with experimental results.

DETAILED DESCRIPTION

Figure 1A:
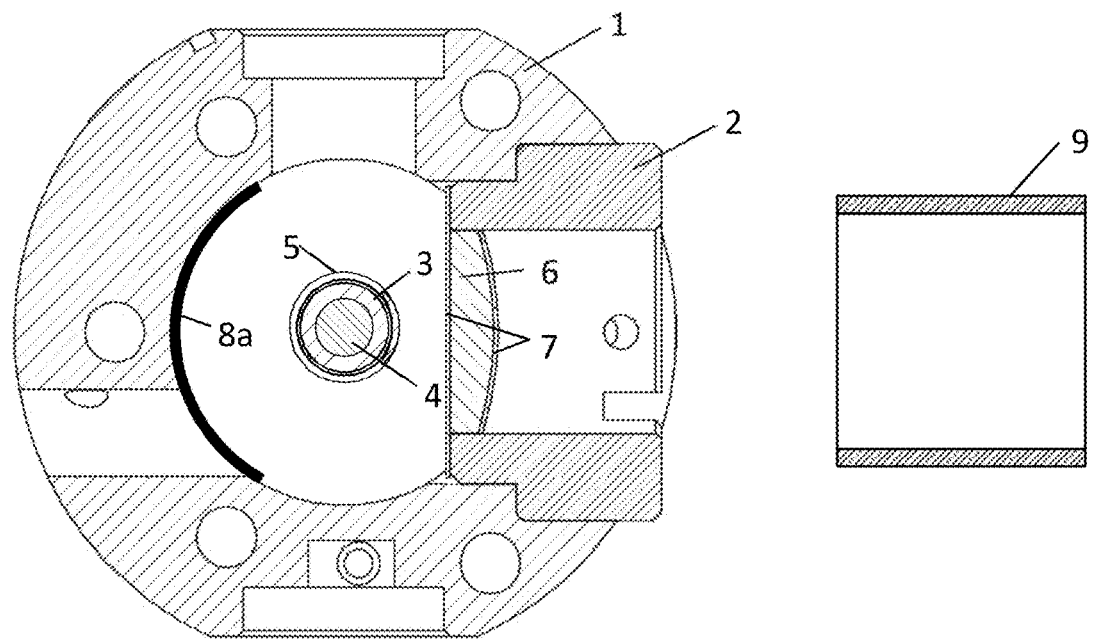
FIG. 1A shows a schematic cross-sectional illustration of a first embodiment of the NMR-MAS probe head according to the invention, comprising a microwave mirror securely attached to the stator inner wall.
Figure 1B:
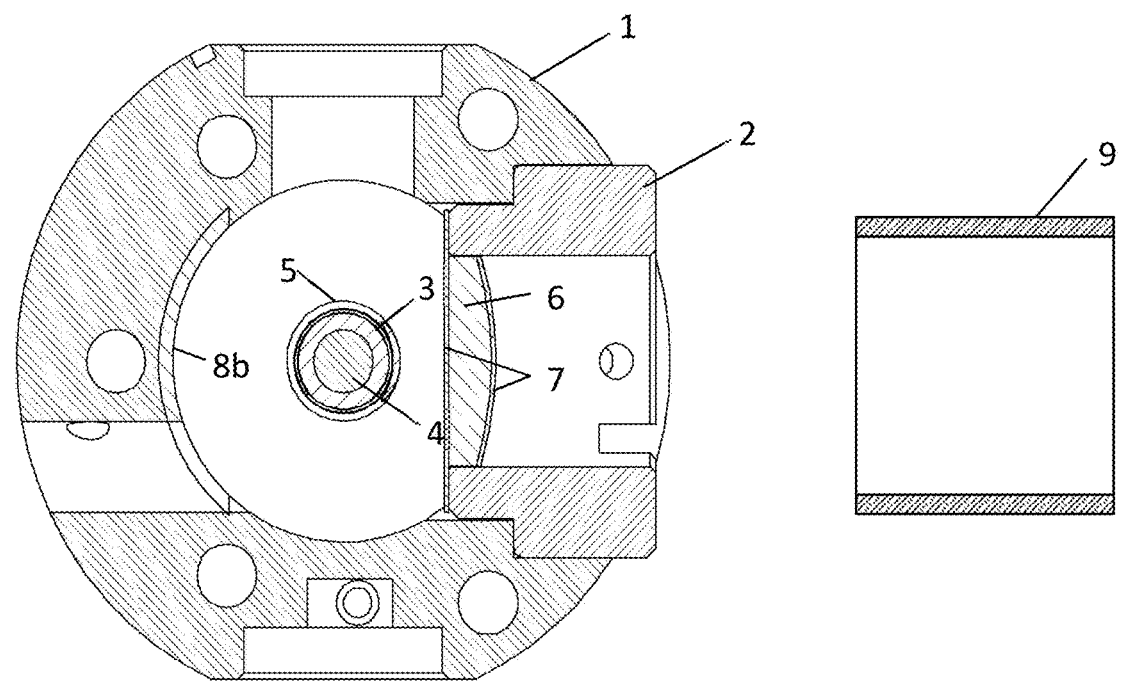
FIG. 1B shows a further embodiment of the invention with an adjustable microwave mirror.

The invention relates to a novel configuration of an MAS stator for an MAS-DNP-NMR probe head and the principal application thereof is as a constituent of a magnetic resonance apparatus. The embodiments of the arrangement according to the invention, as depicted in FIGS. 1A and 1B, each comprise an MAS stator 1 of an NMR probe head for receiving a substantially circular-cylindrical hollow MAS rotor 3 with a sample substance in a sample volume 4, which MAS rotor may be mounted on pressurized gas in a measuring position within the MAS stator 1 with a device for gas supply and set into rotation about the cylinder axis of the MAS rotor 3 with of a pneumatic drive, wherein provision is made of a hollow microwave guide 9 for supplying microwave radiation into the sample volume 4 through an opening in a coil block 2 introduced into the wall of the MAS stator 1, wherein a microwave lens 6 is arranged between the microwave guide 9 and the sample volume 4 for focusing the supplied microwave radiation onto the MAS rotor 3, wherein the MAS rotor 3 is surrounded by a solenoid RF coil 5 and wherein a microwave mirror 8a; 8b for reflecting the microwave radiation emerging from the microwave guide 9 and passing through the sample volume 4 is present on the inner side of the MAS stator 1 lying opposite the microwave guide 9.

The arrangement according to the invention is distinguished by virtue of the microwave lens 6 being arranged in the opening of the coil block 2 on the side facing the sample volume 4 and geometrically embodied in respect of the focal length thereof in such a way that the cylinder axis of the MAS rotor 3 lies in the focus of the microwave lens 6.

The microwave lens 6 has a geometric embodiment such that the thickness thereof on the central axis thereof is an integer multiple of half the wavelength of the transmitted microwave radiation in the dielectric of the microwave guide 9 such that the microwave radiation incident from the microwave guide 9 is transmitted maximally in the direction toward the sample volume 4.

The RF coil 5 is a single-layer solenoid coil constructed from a plurality of spaced-apart windings, the winding wire thickness d and the winding spacing D of which are optimized in such a way that at least 80% of the microwave radiation is transmitted through the RF coil 5, wherein the ratio of d to D is less than or equal to 0.5 and the ratio of D to the wavelength of the microwave radiation in vacuo is greater than 0.5, preferably in the region of 1.

The microwave mirror 8a; 8b is arranged on, or in, the inner wall of the MAS stator 1 lying opposite the microwave guide 9 in respect of the sample volume 4 and is constructed cylindrically and in concave fashion in the direction toward the sample volume 4. Moreover, from a structural point of view, the microwave mirror 8a; 8b is configured in such a way that it focuses the microwave radiation which comes from the sample volume 4 and is incident on said mirror onto the central axis of the circular-cylindrical MAS rotor 3.

An antireflection coating 7 preferably made of plastic, in particular made of PTFE or Vespel, or made of a sub-wavelength structure may be applied to the outer surfaces of the microwave lens 6 in the case of the MAS stator 1 according to the invention.

In the first embodiment of the invention in accordance with FIG. 1A, the microwave mirror 8a is rigidly applied, in particular adhesively bonded, soldered or welded, on the inner wall of the MAS stator 1 lying opposite the microwave guide 9 in respect of the sample volume 4.

In the further embodiment of the invention depicted in FIG. 1B, the microwave mirror 8b is introduced in adjustable, in particular displaceable, fashion into the inner wall of the MAS stator 1 lying opposite the microwave guide 9 in respect of the sample volume 4.

Figure 2A:
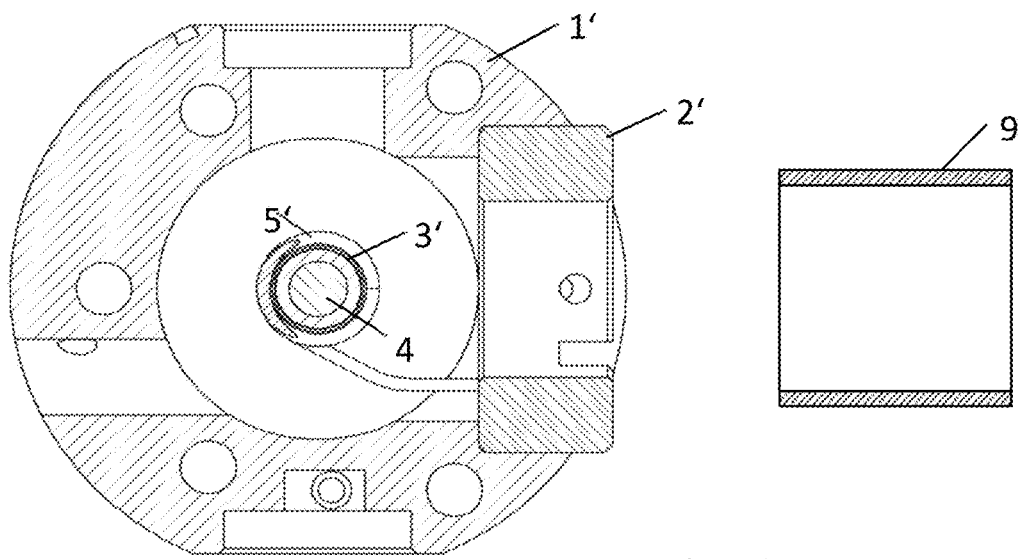
FIG. 2A shows a schematic cross-sectional illustration of an NMR-MAS probe head according to the prior art, without microwave lens and without microwave mirror.
Figure 2B:
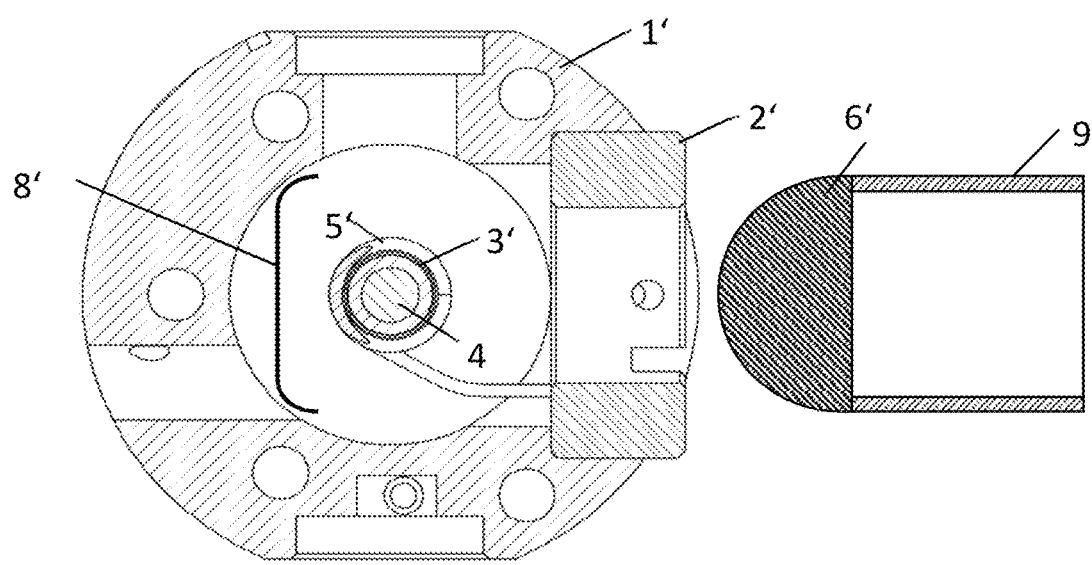
FIG. 2B shows a schematic cross-sectional illustration of an NMR-MAS probe head according to the closest prior art, comprising a planoconvex microwave lens and a flat microwave mirror.

For improved understanding, the previously conventional technology, as depicted in FIGS. 2A and 2B and as now improved by the invention, is to be explained below:

An MAS stator 1', a coil block 2', an MAS rotor 3' with a sample substance in the sample volume 4, an RF coil 5' and a hollow microwave guide 9' are also present in each case in the arrangements in accordance with the prior art. The arrangement in FIG. 2B moreover also comprises a microwave lens 6' and a microwave mirror 8.

In the prior art according to FIG. 2A, the incident microwave beam is merely directed onto the sample volume; it is not modified in any way apart from being matched in terms of size to the sample. A significant portion of the power is lost upon incidence on the coil and rotor as a result of scattering, diffraction and reflection. The present invention uses the beam more skillfully by virtue of the beam characteristic being largely maintained and the beam passing through the sample again as a result of reflection.

The closest prior art likewise uses a lens and a mirror and a possible embodiment is shown in FIG. 2B. However, according to FIG. 10C, the lens has a spherical embodiment, at least in the direction parallel to the rotor axis, while the present invention describes a lens area which is curved in an orthogonal direction in relation to the rotor axis. Therefore, it is unclear from this closest prior art how the cylindrical property of the rotor is taken into account. Moreover, FIG. 10C shows structures and distances which are only slightly larger than one wavelength. It is significantly easier to produce a resonant structure in this design. The present invention optimizes the prior art for a case where the characteristic size of the structure is several (>10) wavelengths.

The optimization of the irradiation according to the invention is carried out by the cylindrical lens 6 so as to obtain a perpendicular angle of incidence onto the rotor 3 and for focusing onto the rotor. In the case of perpendicular incidence on the rotor wall, the actually curved rotor wall acts like a wall with a constant thickness which may be optimized for maximum transmission. If this is not carried out, the beam is incident at a different angle on the rotor depending on the distance from the center, and so the transmitted part of the beam varies dependent upon position and it is not possible to uniformly maximize the intensity thereof In this respect, this constitutes a restriction to the obvious function of the lens, namely that of focusing the beam onto the sample. The focal length of the lens must correspond to the distance of the lens from the rotor/coil center.

The lens made of dielectric material has dimensions which are of the same order of magnitude as the wavelength of the introduced mm wave. Accordingly, the thickness of the lens influences the intensity of the transmitted wave. Firstly, this is due to damping in the dielectric, as a result of which the transmission continuously decreases with increasing thickness. In the case of low-loss dielectrics, such as e.g. sapphire, this portion may lie under 1%. Moreover, the transmission exhibits a periodic dependence on the thickness. This is due to the interference of the beam components reflected and transmitted at the two interfaces of the lens. As an approximation, the assumption should be made that only the thickness of the lens at the center is considered since the maximum of the intensity of the Gaussian beam is also situated there. On account of constructive interference, the transmission through the lens is at a maximum if the thickness thereof is $m \cdot \lambda_m/2$, where m is an integer >1 and $\lambda_m = \lambda_0/\sqrt{(\varepsilon_r)}$ is the wavelength in the dielectric, determined by the wavelength in the vacuum divided by the square root of the relative permittivity of the lens material. Minimums of transmission emerge for lenses with a thickness of $(2m+1) \cdot \lambda_m/4$. This is particularly relevant if a lens is used without an antireflection coating. If antireflection coatings are used on both sides of the lens, the transmission becomes largely independent of the lens thickness.

Further, a coil adapted in terms of wire diameter and winding spacing in such a way that the transmitted beam is influenced as little as possible (T>80%) is essential to the present invention. The coil winding acts in a manner similar to a polarization filter: the transmission may be optimized for a specific wavelength depending on the thickness of the wire and the spacing D between the individual windings. However, the dependence is nonlinear and analytically describable only with very great outlay already in the case of planar gratings. This relationship is described in the scientific literature.

A cylindrical mirror at the rear wall of the stator for guiding the beam back into the sample while maintaining the Gaussian characteristic is also important for the invention. Preferably, the distance of the mirror is adjustable since the wavelength changes when passing through the sample on account of the different values of permittivity of the material. The reflected wave should not extinguish the arriving one. As a result, the irradiation which, originally, tended to be uncontrolled becomes controlled irradiation with two passages. EM simulations show that this makes the power reducible by a factor of 2-4; first experiments have shown a reduction of 2-3. Simulations have furthermore shown that, in the case of an optimized setup, a good 30% of the introduced power is dissipated in the sample. In the closest prior art, this value lies at approximately 10%. As a result of the higher efficiency, the achievable DNP enhancement is increased even with sources that are weaker than a gyrotron (e.g. klystron).

The modified setup provides different efficiency increases depending on the property of the sample, as there is a dependence on the complex permittivity. Simulation shows that, in the most inexpedient case here, there is a return to the value which would be obtained even without a mirror. This may be remedied here by displacing the mirror in the region of $\lambda/2$ along the beam axis.

At 263 GHz, provision is made for using a 3.2 mm rotor made of sapphire and having an internal diameter of 2.1 mm. The coil is wound from wire with a diameter of 0.3 mm, 7.5 windings and a winding spacing of approximately 1 mm (center to center). The microwave lens 6 has a cylindrical planoconvex embodiment, consists of sapphire, and has a radius of curvature of 11.5 mm and a thickness of approximately 1.5 mm. On one side, an antireflection layer made of Teflon (PTFE) is present, said antireflection coating having a thickness of 0.20 mm and simultaneously also ensuring that the lens does not fall out of the coil block 2. The microwave mirror 8 is embodied as a copper film with a thickness of 70 μm, which has been adhesively bonded to the rear wall of the stator. In this example, the distance between the mirror and the rotor center is 6 mm.

FIG. 3 depicts a 3D EM simulation of the H-field amplitude in the case of an arrangement according to the closest prior art (top) and an arrangement according to the invention (bottom). By means thereof, the technical progress on account of the present invention is clearly elucidated:

Existing Case (Prior Art, Top):

The Gaussian beam arrives from the right and is incident on the coil and rotor; although the illumination is quite good, the beam is reflected and diffracted in an uncontrolled manner after the first incidence, as a result of which a significant part is lost.

Invention (Bottom):

The Gaussian beam arrives from the right, is incident on the cylindrical lens and is focused in one direction such that it is incident in virtually perpendicular fashion on the rotor. As a result, the rotor wall may be adapted uniformly since the rotor then does not act like a curved area but like a plane dielectric instead. The coil transmits the beam in a largely unimpeded fashion such that said beam is reflected at the cylindrical mirror and passes through the sample again. The two-fold passage increases the amount of power taken up in the sample.

The increase in efficiency on account of the invention is graphically depicted in FIG. 4 in an exemplary manner. From the experimental data assembled in FIG. 4, it is possible to identify how the stator according to the invention or the rotor according to the invention behaves in respect of the polarization gain (DNP gain) as a function of the incoming microwave power in different combinations with a standard rotor or standard stator as used until the present. Here, it is clearly possible to identify that the stator alone already improves the "DNP gain". The combination of stator and rotor according to the invention leads to the same polarization effect already being obtained at significantly lower microwave power (3.6 W instead of 8.7 W). Thus, as a consequence, it is possible to resort to smaller and more cost-effective microwave sources. If the provided power is not limited, a higher DNP gain may, under certain circumstances, also be obtained in saturation.

LIST OF REFERENCE SIGNS

1; 1' MAS stator
2; 2' Coil block
3; 3' MAS rotor
4 Sample volume
5; 5' RF coil
6; 6' Microwave lens
7 Antireflection coating
8a; 8b; 8' Microwave mirror
9 Microwave guide

What is claimed is:

1. A nuclear magnetic resonance (NMR) probe head, comprising:
    a Magic Angle Spinning (MAS) stator comprising a coil block introduced into a wall of the MAS stator,
    a substantially circular-cylindrical hollow MAS rotor having a cylinder axis and configured to receive a sample substance in a sample volume and to be mounted with pressurized gas from a gas supply in a measuring position within the MAS stator rotatably about the cylinder axis of the MAS rotor through a pneumatic drive, wherein the MAS rotor is surrounded by a solenoid radio frequency (RF) coil,
    a hollow microwave guide configured to supply microwave radiation into the sample volume through an opening in the coil block,
    a microwave lens arranged between the microwave guide and the sample volume, and configured to focus the supplied microwave radiation onto the MAS rotor, and
    a microwave mirror configured to reflect the microwave radiation from the microwave guide after passing through the sample volume, and arranged on or in an inner wall of the MAS stator opposite the microwave guide,
    wherein the microwave lens has a focal length and is arranged in an opening of the coil block on a side facing the sample volume such that the cylinder axis of the MAS rotor lies in the focus of the microwave lens,
    wherein the RF coil is a single-layer solenoid coil constructed from a plurality of spaced-apart windings, a winding wire thickness d and a winding spacing D of which are configured such that at least 80% of the microwave radiation is transmitted through the RF coil, wherein the ratio of the winding wire thickness d to the winding spacing D is less than or equal to 0.5 and the ratio of the winding spacing D to a wavelength of the microwave radiation in vacuo is greater than 0.5,
    wherein the microwave mirror is arranged on or in the inner wall of the MAS stator opposite the microwave guide with respect to the sample volume and is constructed cylindrically and concavely in the direction toward the sample volume, and
    wherein the microwave mirror is configured to focus the microwave radiation from the sample volume and incident on said the microwave mirror onto the central axis of the circular-cylindrical MAS rotor.

2. The probe head as claimed in claim 1, wherein the microwave lens is configured to have a thickness on a central axis of the microwave lens that is an integer multiple of half the wavelength of the microwave radiation transmitted in a dielectric of the microwave guide such that the microwave radiation from the microwave guide is transmitted maximally toward the sample volume.

3. The probe head as claimed in claim 1, wherein the microwave lens is planoconvex as seen in a beam direction of the microwave radiation emerging from the microwave guide toward the sample volume.

4. The probe head as claimed in claim 3, wherein the microwave lens has a thickness of between 1 mm and 2 mm on the central axis of the microwave lens.

5. The probe head as claimed in claim 1, wherein the microwave lens has at least one cylindrical area.

6. The probe head as claimed in claim 5, wherein the at least one cylindrical area has a radius of curvature of between 8 mm and 15 mm.

7. The probe head as claimed in claim 1, wherein the microwave lens is constructed from sapphire and/or silicon and/or boron nitride and/or a further dielectric material.

8. The probe head as claimed in claim 1, wherein the microwave lens comprises an antireflection coating applied to at least one outer surface of the microwave lens.

9. The probe head as claimed in claim 8, wherein the antireflection coating comprises PTFE or Vespel, or comprises a sub-wavelength structure.

10. The probe head as claimed in claim 1, wherein the RF coil is constructed from a magnetically compensated wire, or from Cu and/or Ag and/or Al, or from alloys thereof.

11. The probe head as claimed in claim 1, wherein the RF coil is constructed with a winding wire thickness d of 0.2 mm to 0.5 mm, with 5 to 10 windings, and with a winding spacing D of 0.7 mm to 2 mm.

12. The probe head as claimed in claim 1, wherein the microwave mirror is constructed from Ag, Au or Cu sheet.

13. The probe head as claimed in claim 12, wherein the microwave mirror has a thickness between 1 μm and 100 μm.

14. The probe head as claimed in claim 1, wherein the microwave mirror is rigidly applied onto the inner wall of the MAS stator opposite the microwave guide with respect to the sample volume.

15. The probe head as claimed in claim 14, wherein the microwave mirror is rigidly applied onto the inner wall with an adhesive bond, a solder or a weld.

16. The probe head as claimed in claim 1, wherein the microwave mirror is displaceably mounted onto or into the inner wall of the MAS stator opposite the microwave guide with respect to the sample volume.

17. The probe head as claimed in claim 1, further comprising a pneumatic sample interchange system configured to guide the MAS rotor to and from the MAS stator.

18. The probe head as claimed in claim 17, wherein the MAS rotor has a diameter of between 0.7 mm and 4 mm.

19. The probe head as claimed in claim 17, wherein the hollow MAS rotor is configured to have a wall thickness that corresponds to an integer multiple of half the wavelength of the microwave radiation transmitted in a dielectric of the rotor wall such that the microwave radiation from the microwave lens is transmitted maximally toward the sample volume, out of the sample volume and onto the microwave mirror.

20. The probe head as claimed in claim 17, wherein the MAS rotor is constructed from sapphire, tetragonally stabilized zirconium oxide and/or silicon nitride.

21. The probe head as claimed in claim 17, wherein the MAS rotor has a wall thickness between 0.2 mm and 0.7 mm and has a diameter of less than 4 mm.

* * * * *